US005173260A

United States Patent [19]
Zander et al.

[11] Patent Number: 5,173,260
[45] Date of Patent: Dec. 22, 1992

[54] BEADS FUSED TO A TEST DEVICE SUPPORT

[75] Inventors: Dennis R. Zander, Penfield; Richard C. Sutton, Rochester, both of N.Y.

[73] Assignee: Eastman Kodak Company, Rochester, N.Y.

[21] Appl. No.: 639,454

[22] Filed: Jan. 10, 1991

Related U.S. Application Data

[63] Continuation-in-part of Ser. No. 583,106, Sep. 17, 1990, abandoned.

[51] Int. Cl.$^5$ .................. B01L 3/00; C12Q 1/68; C12N 11/02; C12M 1/00
[52] U.S. Cl. .................. 422/57; 422/61; 422/99; 435/6; 435/174; 435/177; 435/180; 435/287; 435/288; 436/528; 935/77; 935/85
[58] Field of Search .................. 422/56, 61, 57, 99; 435/6, 174, 177, 180, 287, 288; 436/519, 523, 524, 528, 531; 935/76, 77, 85

[56] References Cited

U.S. PATENT DOCUMENTS

| | | | |
|---|---|---|---|
| 4,258,001 | 3/1981 | Pierce et al. | 422/56 |
| 4,430,436 | 2/1984 | Koyama et al. | 436/531 |
| 4,654,299 | 3/1987 | Lentfer | 436/531 |
| 4,663,277 | 5/1987 | Wang | 436/531 |
| 4,837,162 | 6/1989 | Rothman et al. | 436/531 |
| 4,921,878 | 5/1990 | Rothman et al. | 436/531 |

FOREIGN PATENT DOCUMENTS 381501 8/1990 European Pat. Off. .

Primary Examiner—James C. Housel
Assistant Examiner—William Chan
Attorney, Agent, or Firm—Dana M. Schmidt

[57] ABSTRACT

A test device comprising beads with a reagent attached, the beads being physically fused to a support. The support includes a material selected to have a melting temperature significantly lower than that of the beads. Polyehtylene is a preferred example of such a material.

5 Claims, 1 Drawing Sheet

U.S. Patent  Dec. 22, 1992  5,173,260 ously 5,173,260

BEADS FUSED TO A TEST DEVICE SUPPORT

RELATED APPLICATIONS

This is a continuation-in-part application of U.S. Ser. No. 583,106 filed on Sep. 17, 1990, now abandoned.

FIELD OF THE INVENTION

This invention concerns the attachment of test beads bearing a reagent, so that they are not washed away by the test sample liquid.

BACKGROUND OF THE INVENTION

Detection devices can use a bead layer mounted on a support, wherein reagents are bonded to the beads to react with a sample. In many such devices, liquid flows perpendicularly into the layer so that flow occurring ACROSS the layer, such as could wash off beads inadequately adhered, is minimized.

However, in some environments, particularly qualitative detection of DNA, it is preferred that the sample liquid being analyzed flow-by, rather than through, the bead layer, for the desired reaction with the beads used for detection. In such a case, the flow-by of the liquid will wash off any beads that are not securely attached. If enough of the beads wash off, there will be insufficient numbers remaining to produce a visible signal that indicates the target DNA is present. For example, no color will generate even though the targeted DNA had been replicated or was present. It is possible to anchor beads against washoff, by using as their support, a latex-coated paper. However, the use of a paper support creates manufacturing disadvantages. The paper with the beads pre-attached must be carefully transported to the device's detection chamber, where it must be fixed in place. A more preferred method would be to somehow place the beads directly onto the material comprising the detection chamber, which can be polyethylene. This, however, has not been readily possible, since simply drying the beads in place on such a material, from an aqueous solution, provides insufficient anchoring of the beads when the sample to be detected flows by.

Accordingly, prior to this invention there has been a need to anchor detection beads to a support in a manner that is more convenient, that is, does not require an interim support other than the wall of the detection chamber.

SUMMARY OF THE INVENTION

We have constructed a test device that anchors the beads sufficiently to meet the above-noted need.

More specifically, there is provided a test device comprising inert beads to which reagents are attached, and an inert support on which the beads are disposed to react with a test sample liquid, the support and beads comprising different materials. The device is improved in that support is physically fused to at least some of the beads, and the material of the support is selected to have a significantly lower melting point than the material of the beads, so that the fused beads cannot be washed off the support by the test sample liquid.

Accordingly, it is an advantageous feature of the invention that a flow-by test device is provided with beads that are anchored directly to the wall of the detection chamber.

It is a related advantageous feature of the invention that a flow-by test device is provided using simplified manufacturing procedures.

Other advantageous features will become apparent upon reference to the following detailed Description of the Preferred Embodiments, when read in light of the attached drawings.

DESCRIPTION OF THE PREFERRED EMBODIMENTS

The invention is hereinafter described in connection with a pouch test device for qualitatively detecting the presence of replicated DNA by the use of certain beads having thereon certain immobilizing groups that anneal to DNA as it flows by the beads. In addition, the invention is useful even if the test device is not a pouch, regardless whether DNA or some other target is being detected, and even regardless whether or not the immobilizing of the target occurs for detection purposes or some other purpose. Also, it is useful regardless of the chemical nature of the beads and/or the immobilizing groups, provided the beads have an appropriate melting point as in hereinafter explained.

Figure 1:
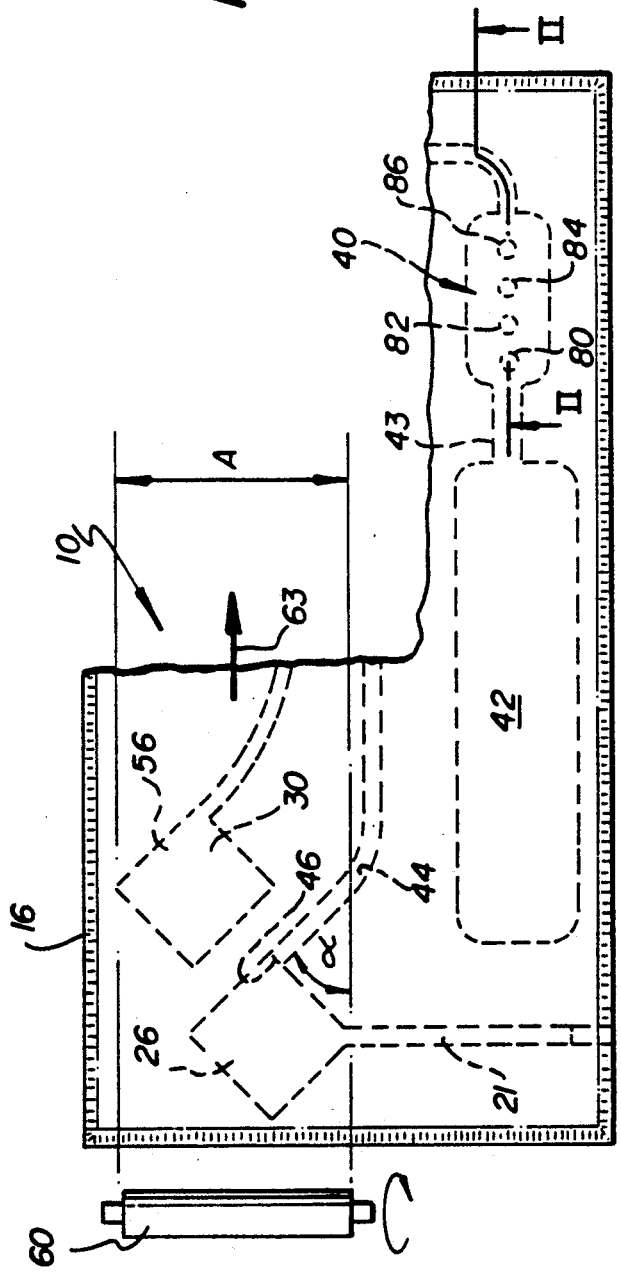
FIG. 1 is a fragmentary plan view of a cuvette pouch constructed in accordance with the invention.

As shown in FIG. 1, the preferred device is a pouch 10, which cooperates with an external source of pressure 60 to transfer liquid within the pouch. As described in commonly owned EPA publication 381,501, by Schnipelsky et al, entitled "Containment Cuvette for PCR and Method of Use", such a device is intended primarily for use with PCR amplification to generate enough replicates of a particular DNA as to render detectable that such DNA is present. More particularly, the device is a containment cuvette constructed to be completely closed after sample introduction occurs, so that no leak of target DNA can occur during or after amplification such as would contaminate nearby pouches yet to be supplied with sample.

Figure 2:
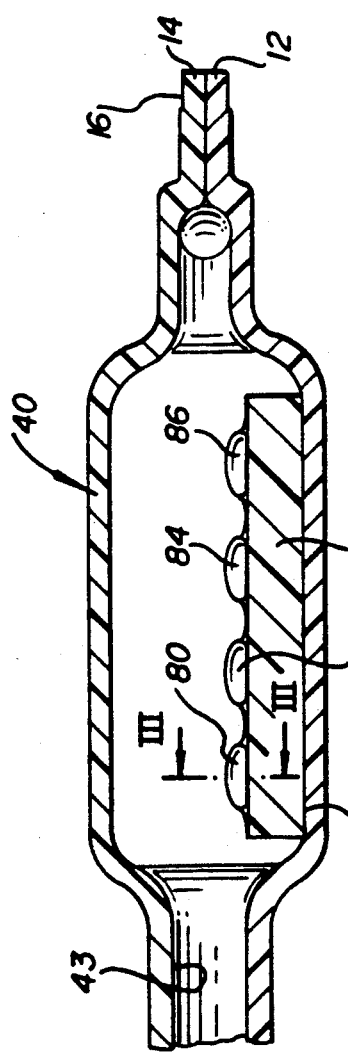
FIG. 2 is a section view taken generally along the line II—II of FIG. 1.

Thus, cuvette 10 comprises two relatively thin sheets 12, 14, FIG. 2, formed such as by molding to mate together with pockets or compartments and connecting passageways protruding from the plane of the contacting sheets, FIG. 2. The sheets are secured together at least along their outer periphery 16, FIG. 1, and preferably at all points surrounding compartments or passageways, such as by heat- and/or ultrasonic pressure-sealing. A heat-activatable adhesive such as polyethylene-co-vinyl acetate is useful for such joining operation.

The compartments are as follows: compartment 26 is the reaction compartment, and optionally has amplifying reagents pre-incorporated therein, in liquid or dried form. DNA sample is injected via passageway 21 which is then sealed. Compartment 30 is a storage compartment containing wash water as a pre-incorporated reagent. Other compartments, not shown, provide a) a storage compartment containing at least one of the detection materials pre-incorporated therein, namely a biotinylated probe having at one end a complementary nucleotide for attachment to the amplified DNA, and preferably also a signal generating moiety, for example, avidin bound to the horseradish peroxidase; b) a second wash-containing storage compartment, which preferably has a much larger volume that the volume of the first-mentioned storage compartment; c) a storage compartment having pre-incorporated therein, detection reagents, namely a peroxide and leuco dye, for example 2-(4-hydroxy-3,5-dimethoxyphenyl)-4,5-bis(4-methoxyphenyl)imidazole, preferably in combination with poly(vinyl pyrrolidone) as a stabilizer; and d) optionally, a storage compartment having pre-incorporated therein a stop solution to prevent too much leuco dye from converting to the dye, for example, pure water. Since these reagents are well known, further explanation is not needed.

Compartment 40, FIG. 1, is the detection site for this embodiment, discussed hereinafter, and compartment 42 is the waste compartment, preferably initially deflated to provide for expansion as liquid is forced into it. Compartment 42 connects to compartment 40 via passageway 43. Optionally, a one-way check valve (not shown) can be included in passageway 43 to prevent waste liquid from backwashing into compartment 40, thus creating undesirable background color.

Besides passageway 21, the interconnections are as follows: passageway 44 connects reaction compartment 26 with detection compartment 40, except that a temporary seal is provided at 46 to keep introduced DNA in compartment 26 until pressure is generated by roller 60. Other passageways, not shown, connect the other compartments, not shown, all with detection compartment 40, each preferably with a temporary seal 46 or 56, that prevents flow out of the respective compartment until roller 60 breaks the seal. One passageway serves as the trunk line to which the others are joined.

The compartments are deliberately positioned, FIG. 1, so that each one will empty into compartment 40 in the proper sequence as roller 60 advances along path A in the direction of arrows 63. Thus, first the amplified DNA is pushed into compartment 40, then the first wash, then the detection probe from its compartment, then the second wash, then the leuco dye solution and finally the stop solution. In some cases, the development of the dye from the leuco dye is done in the dark, for example, if the dye should fade readily in light. The respective passageways are also preferably constructed so as to be squeezed by the roller—that is, they are constructed to always form an angle alpha to arrows 63 that is less than a right angle, within path A. If they were to form a right angle, the roller would tend to jump over the passageway, rather than squeeze it.

It is not essential that both sheets 12 and 14, FIG. 2, be collapsible by roller 60—only that at least one of them be, under a pressure of at least 170 g/cm. Pressures as high as 1500 g/cm are also useful. Thus, sheet 12 can comprise a collapsible, relatively flexible plastic such as a heat-sealable polyester, for example, Scotchpak TM brand heat-sealable film no. 229 made by 3M, whereas sheet 14 can be less flexible and less collapsible, or it can be of the same flexibility as sheet 12.

At least for compartment 26, sheet 14 can comprise a laminate of an aluminum foil on the outside and a polymer layer on the inside, preferably a layer of polyester, like sheet 12. The aluminum foil preferably has a thickness of between about 0.0013 cm and about 0.026 cm, and most preferably about 0.005 cm. The polymer layer has a thickness of between about 0.0013 cm and about 0.03, and most preferably about 0.005 cm. The advantage of the laminate construction over a single sheet of plastic is that, once the compartment is crushed by the roller, the aluminum resists reinflation such as could allow backwashing to occur from liquids under pressure downstream. For this reason, sheet 14 is preferably so constructed as a laminate for the entire length of cuvette 10.

It is preferred that a liquid, when ejected from its compartment, not backwash up to the passageway used to empty another compartment that is further downstream. To this end, as roller 60 advances from left to right, FIG. 1, pinching means, e.g., a compression roller, (not shown) can be used to descend onto cuvette 10 to pinch off the passageways.

Alternatively, a prewash compartment can be included, not shown, to insure that all the exit passageways are first filled with water, so that upstream compartments will not backwash into the passageways for downstream compartments.

For detection purposes, chamber 40 includes means anchored to a support 70, FIG. 2, for immobilizing amplified DNA, which, when immobilized, can react with a label to produce a detectable signal, such as a color change. Preferably, such means are one or more piles of beads 80, 82, 84 and 86, FIG. 1, (most preferably, three piles), the beads having attached thereto certain chemicals. The most preferred form of the beads is one in which an immobilizing probe only, is attached to the bead. A detection probe then attaches to the immobilized, targeted DNA, for use with one or more detection reagents. More specifically, the beads have an oligonucleotide bonded to the bead via a chemical link, such nucleotide being effective to anneal to a portion of the targeted DNA, either at room temperature or with slight heating. Useful oligonucleotides are selected depending on the targeted DNA of choice, and include, for example, the sequences 5'-ATC-CTG-GGA-TTA-AAT-AAA-ATA-GTA-AGA-ATG-TAT-AGC-CCT-AC-3'. Any chemical link and bead polymer is useful to bond the oligonucleotide to the bead. For example, tetraethylene-amine dioles can be used, wherein the amine group reacts with pendent carboxylic acid groups on the bead. To provide such carboxylic acid groups, an appropriately modified styrene polymer or copolymer is preferably used. Highly preferred is a bead formed from a copolymer of styrene (about 98 mole percent) and a carboxylic acid-modified styrene (about 2 mole percent) such as 3-(p-vinylbenzylthio)propionic acid. Such beads have a melt temperature that is about 240° C.

The replicated target sequences have biotin bonded to the target DNA. The biotin then reacts with avidin that is pre-attached to a strep-horseradish peroxidase enzyme, one of the detection reagents provided in a storage chamber of cuvette 10. The other detection reagents include a substrate that will react with the peroxidase to generate a color, as noted above.

Figure 3:
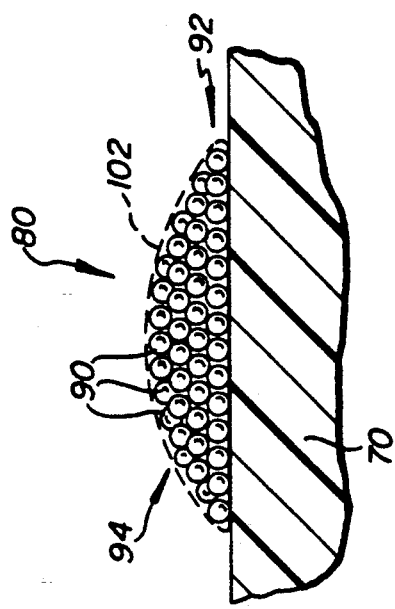
FIG. 3 is an enlarged partially schematic section view taken generally along the line III—III of FIG. 2.

Each pile 80, 82, 84 and 86 comprises a plurality of beads 90, FIG. 3. In accordance with the invention, at least some of the beads of each pile are fused to the support 70, from a buffer solution. To ensure that a minimum, and preferably no, denaturing occurs to the oligonucleotide on the beads, support 70 is preferably selected from a plastic having a melting point that is significantly (i.e., at least 20° C.) less than that of the beads. Most preferably, that heating temperature is selected to be less than 150° C., as this gives maximum insurance against denaturing the oligonucleotides on the beads. A highly useful plastic meeting this requirement is polyethylene, although others having such a melting point less than 150° C. are useful also. Most preferably, support 70 is such a layer of polyethylene, laminated onto a very thin layer of poly(ethylene terephthalate) (PET) to facilitate the application of heat. That is, by heating the backside of the PET, heat can be diffused through to the polyethylene without unduly weakening support 70. Useful thicknesses of the support include, e.g. 89 microns of polyethylene and 13 microns of PET.

The fusion of beads 90 to support 70 is readily done by depositing a 1% aqueous buffer suspension of the beads at the desired defined area, using a 0.1 molar concentration of a buffer comprising glycine at a pH of 8.5, containing 0.01% Thimerosal. This solution is then heated as follows: a heating iron is applied to the underneath surface 100, FIG. 2, using a temperature setting sufficient to render the polyethylene tacky. For example, a temperature of about 110° C. at the tip is useful. The tacky condition is sufficient to fuse the beads. A useful example is a heating iron available under the tradename EC 2001 ESD from Weller.

Microphotos of the result show a structure as illustrated in FIG. 3. At least the lower layer 92 of beads can be seen to have polyethylene that has wetted and sealed to those beads of layer 92. It is not clear that the plastic of support 70 has also wetted the upper layers, although there does appear to be some adhesion of the upper layers of beads to layer 92, by a mechanism not understood. That is, a layer perhaps of the buffer salts does appear coated over all the upper layers, as suggested by the dashed layer 102, FIG. 3. This is clearly not polyethylene, however, as layer 102 washes away when the sample solution passes by, leaving the structure shown in FIG. 3 without the layer 102.

When such a pile of beads was used to actually test for a targeted DNA, enough of the beads remained after the solution flowed past it, to produce a clear color stronger than any background signal on the support away from piles 80, 82, 84 or 86.

As a comparison example, an aqueous solution of the same beads was applied identically as described above, except that no buffer was present. When the heating iron was applied, too much heat appeared to be delivered, as the beads seemed to fuse/melt together to form a permanent overlayer of polyethylene somewhat analogous to layer 102, which, however, would not wash away. Furthermore, these beads are not capable of immobilizing targeted DNA, which indicates that either the oligonucleotides on the beads were denatured, or melting occurred so much that the oligonucleotides were covered up. This comparison example suggests that the presence of the buffer salt is needed if fusion is done in this manner. However, it has been shown that the buffer salts (layer 102) can be washed away and the beads still function. Thus, the buffer is not needed in the test device for detection.

It will be readily appreciated that such anchoring of the beads is preferably achieved without the use of an adhesive composition, that is, without the use of a material different from the support or the beads to bind the beads to the support. Whatever mechanism is binding upper bead layers 94 to lower bead layer 92, we have found that, if fusion is not done by melting the support to the beads, substantially all the beads wash away even though the buffer salt may have been present.

The invention has been described in detail with particular reference to preferred embodiments thereof, but it will be understood that variations and modifications can be effected within the spirit and scope of the invention.

What is claimed is:

1. In a test device comprising inert beads to which reagents are attached, and an inert support on which said beads are disposed to react with a test sample liquid, the support and beads comprising different materials;

the improvement wherein said support is attached to said beads solely by being physically melt-fused to at least some of said beads, said material of said support being selected to have a melting point which is at least 20 degrees C. less than that of said material of said beads, so that the fused beads cannot be washed off the support by the test sample liquid.

2. A test device as defined in claim 1, wherein said beads comprise a styrene copolymer and said support comprises polyethylene.

3. A test device as defined in claim 1, wherein said melting point of said support is less than 150° C., and said reagents on said beads comprise an oligonucleotide, so that said support can be melted without denaturing said oligonucleotide.

4. A test device as defined in claims 1, 2 or 3, and further including, in the device, indicator reagents for polymerase chain reaction amplification comprising a label.

5. A test device as defined in claim 2, wherein said support comprises a laminate of polyethylene and polyethylene terephthalate.

* * * * *